(12) United States Patent
Zhu et al.

(10) Patent No.: US 9,301,425 B2
(45) Date of Patent: Mar. 29, 2016

(54) CHILLER-LESS COOLING SYSTEM AND METHOD FOR INTERVENTIONAL DETECTOR

(71) Applicant: GE MEDICAL SYSTEMS GLOBAL TECHNOLOGY COMPANY, LLC, Waukesha, WI (US)

(72) Inventors: Weihua Zhu, Beijing (CN); Qingming Peng, Beijing (CN)

(73) Assignee: GE MEDICAL SYSTEMS GLOBAL TECHNOLOGY COMPANY, LLC, Waukesha, WI (US)

( * ) Notice: Subject to any disclaimer, the term of this patent is extended or adjusted under 35 U.S.C. 154(b) by 0 days.

(21) Appl. No.: 14/051,861

(22) Filed: Oct. 11, 2013

(65) Prior Publication Data

US 2014/0104789 A1 Apr. 17, 2014

(30) Foreign Application Priority Data

Oct. 12, 2012 (CN) .......................... 2012 1 0385984

(51) Int. Cl.
*G01T 1/24* (2006.01)
*H05K 7/20* (2006.01)
*A61B 6/00* (2006.01)

(52) U.S. Cl.
CPC .............. *H05K 7/20336* (2013.01); *A61B 6/42* (2013.01); *A61B 6/4208* (2013.01); *A61B 6/4233* (2013.01); *A61B 6/4429* (2013.01); *A61B 6/4441* (2013.01); *A61B 6/4452* (2013.01); *A61B 6/4488* (2013.01); *H05K 7/20409* (2013.01)

(58) Field of Classification Search
USPC .................................................. 250/370.15
See application file for complete search history.

(56) References Cited

U.S. PATENT DOCUMENTS

| 6,007,243 A * | 12/1999 | Ergun et al. .................... 378/197 |
| 2003/0085359 A1* | 5/2003 | Dailey et al. .............. 250/370.15 |
| 2007/0221859 A1 | 9/2007 | Nakata |
| 2009/0084969 A1* | 4/2009 | Ohta et al. ............... 250/370.15 |

FOREIGN PATENT DOCUMENTS

| EP | 0943931 A2 | 9/1999 |
| JP | 2010259577 A | 11/2010 |
| WO | 2007086591 A1 | 8/2007 |

OTHER PUBLICATIONS

European Search Report and Written Opinion issued in connection with corresponding EP Application No. 13187845.6 on Apr. 22, 2014.

* cited by examiner

*Primary Examiner* — David Porta
*Assistant Examiner* — Edwin Gunberg
(74) *Attorney, Agent, or Firm* — GE Global Patent Operation; Marc A. Vivenzio

(57) ABSTRACT

A chiller-less cooling system for cooling an interventional detector comprising a detector housing. The detector housing comprising a detector tray to which the detector is attached, a lift frame on which a driving mechanism is installed to lift up/down the detector housing, a connecting arm to connect the detector tray and the lift frame, and a cover. The cooling system comprising a heat pipes connecting the detector tray and the lift frame so as to reduce a thermal resistance between the detector tray and the lift frame and transfer more heat from the detector, an external heat sink connected with the heat pipe for reducing a thermal resistance between the lift frame and an ambient environment, and a high heat transfer coefficient device embedded into the detector tray for collecting heat leading to the heat pipe, obtaining a uniform temperature distribution, and reducing a thermal resistance of the detector tray.

7 Claims, 8 Drawing Sheets

CHILLER-LESS COOLING SYSTEM AND METHOD FOR INTERVENTIONAL DETECTOR

TECHNICAL FIELD

Embodiments of the present invention relate to a cooling system and method for an interventional detector, and, more specifically, to a chiller-less cooling system and method for an interventional detector.

BACKGROUND OF THE INVENTION

In a diagnostic imaging application, image quality is largely affected by detector temperature. Image quality is more critical for vascular application than for other diagnostic imaging modalities due to its unique application. The general thermal requirements about Interventional IQ are listed below:

temperature of detector panel<ambient+5° C.;
temperature change of detector panel<2° C./15 min.

Currently, the detector is cooled by means of cold plate plus chiller (water forced convection). A chiller-less detector for vascular (less power dissipation) is being developed and is the trend in future due to a lot of benefits. In other modalities, such as X-ray radiation, fans are commonly used to blow the detector directly. However, an interventional system has its unique application requirements besides the above two items about temperature, which would affect the thermal design. For example, the patient shall be protected against airflow of particles from system due to fans, or open motors; acoustic noise: the sound pressure level shall be less or equal to 65 dB(A) during X-ray emission and gantry, table or monitor suspension motions; moderate usage: less than 7 exams per day (10 hours of system usage); maximum usage: between 8 and 12 exams per day (10 hours of system usage); and safety requirements in IEC standards about high temperature, such as a max of 41° C. on the surface temperature of an applied part.

Thus, a new cooling path by means of air convection is desirable to replace a traditional chiller cooling system, which must meet the above critical requirements as well.

BRIEF DESCRIPTION OF THE INVENTION

According to an embodiment of the present invention, there is provided a chiller-less cooling method for cooling an interventional detector comprising a detector housing, the detector housing comprising: a detector tray to which the detector is attached; a lift frame on which a driving mechanism is installed to lift up/down the detector housing; a connecting arm to connect the detector tray and the lift frame; and a cover to shield the detector and the components thereof from other external objects, the cooling method comprising: using a heat pipe to connect the detector tray and the lift frame so as to reduce a thermal resistance between the detector tray and the lift frame and transfer more heat from the detector; using an external heat sink connected with the heat pipe so as to reduce a thermal resistance between the lift frame and an ambient environment; and embedding a high heat transfer coefficient device into the detector tray so as to collect heat leading to the heat pipe, obtain a uniform temperature distribution, and reduce a thermal resistance of the detector tray.

In an embodiment, the method further comprises fabricating the heat pipe, the external heat sink and the high heat transfer coefficient device into one thermal module.

According to an embodiment of the present invention, there is provided a chiller-less cooling method for cooling an interventional detector comprising a detector housing, the detector housing comprising: a detector tray to which the detector is attached; a lift frame on which a driving mechanism is installed to lift up/down the detector housing; a connecting arm to connect the detector tray and the lift frame; and a cover to shield the detector and the components thereof from other external objects; the cooling method comprising: using a loop heat pipe as a high-efficiency cooling path to connect the detector tray and a C-arm of an interventional imaging system, the loop heat pipe comprising: a condenser end and an evaporator end; embedding the condenser end of the loop heat pipe into the detector tray; and embedding the evaporator end of the loop heat pipe into a heatspreader which is fixed onto the C-arm; wherein the detector housing and the C-arm can work as two heat sinks in parallel.

In an embodiment, the method further comprises using Al 6063 (thermal conductivity: 200 W/m-K) to fabricate the C-arm.

According to an embodiment of the present invention, there is provided a chiller-less cooling method for cooling an interventional detector comprising a detector housing, the detector housing comprising: a detector tray to which the detector is attached; a lift frame on which a driving mechanism is installed to lift up/down the detector housing; a connecting arm to connect the detector tray and the lift frame; and a cover to shield the detector and the components thereof from other external objects; the cooling method comprising: using a fan/heat sink/loop heat pipe module which is fixed in a C-arm of an interventional imaging system by utilizing an existing pipe structure as a flow tunnel, and hiding a fan of the module in the C-arm, so as to form air forced convection; using a loop heat pipe of the fan/heat sink/loop heat pipe module as a thermal connector between the detector and the C-arm, wherein a condenser end of the loop heat pipe is embedded into the detector tray, and an evaporator end of the loop heat pipe is embedded on a heat sink of the fan/heat sink/loop heat pipe module; and opening an air vent at a proper place on the C-arm where it is safe for a patient.

In an embodiment, method further comprises adjusting speed of the fan per a thermal requirement.

According to an embodiment of the present invention, there is provided a chiller-less cooling system for cooling an interventional detector comprising a detector housing, the detector housing comprising: a detector tray to which the detector is attached; a lift frame on which a driving mechanism is installed to lift up/down the detector housing; a connecting arm to connect the detector tray and the lift frame; and a cover to shield the detector and the components thereof from other external objects; the cooling system comprising: a heat pipes which connects the detector tray and the lift frame so as to reduce a thermal resistance between the detector tray and the lift frame and transfer more heat from the detector; an external heat sink connected with the heat pipe for reducing a thermal resistance between the lift frame and an ambient environment; and a high heat transfer coefficient device embedded into the detector tray for collecting heat leading to the heat pipe, obtaining a uniform temperature distribution, and reducing a thermal resistance of the detector tray.

In an embodiment, the high heat transfer coefficient device can be a vapor chamber or other devices comprising high heat transfer coefficient materials.

According to an embodiment of the present invention, there is provided a chiller-less cooling system for cooling an interventional detector comprising a detector housing, the detector housing comprising: a detector tray to which the detector is attached; a lift frame on which a driving mechanism is installed to lift up/down the detector housing; a connecting arm to connect the detector tray and the lift frame; and a cover to shield the detector and the components thereof from other external objects; the cooling system comprising: a loop heat pipe which connects the detector tray and a C-arm of an interventional imaging system, the loop heat pipe comprising a condenser end and an evaporator end, wherein the condenser end of the loop heat pipe is embedded into the detector tray; the evaporator end of the loop heat pipe is embedded into a heatspreader which is fixed onto the C-arm.

According to an embodiment of the present invention, there is provided a chiller-less cooling system for cooling an interventional detector comprising a detector housing, the detector housing comprising: a detector tray to which the detector is attached; a lift frame on which a driving mechanism is installed to lift up/down the detector housing; a connecting arm to connect the detector tray and the lift frame; and a cover to shield the detector and the components thereof from other external objects; the cooling system comprising: a fan/heat sink/loop heat pipe module which is fixed in a C-arm of an interventional imaging system, the fan/heat sink/loop heat pipe module comprising: a fan which is hidden in the C-arm of the interventional imaging system; a loop heat pipe which is used as a thermal connector between the detector and the C-arm; and a heat sink, wherein a condenser end of the loop heat pipe is embedded into the detector tray, and an evaporator end of the loop heat pipe is embedded into the heat sink; and an air vent which is located at a proper place on the C-arm where it is quite safe for a patient.

BRIEF DESCRIPTION OF THE DRAWINGS

Embodiments of the present invention can be best understood by referring to subsequent description in combination with the drawings, wherein.

DETAILED DESCRIPTION OF THE INVENTION

Embodiments of the present invention provide a cooling system and a method for cooling an interventional detector through air convection without a dedicated chiller, which system and method can efficiently cool the detector, and sufficiently meet all temperature requirements regarding the detector.

According to embodiments of the present invention, chiller-less detector can be applied in other modalities, such as X-ray radiation, and interventional system.

Figure 1:
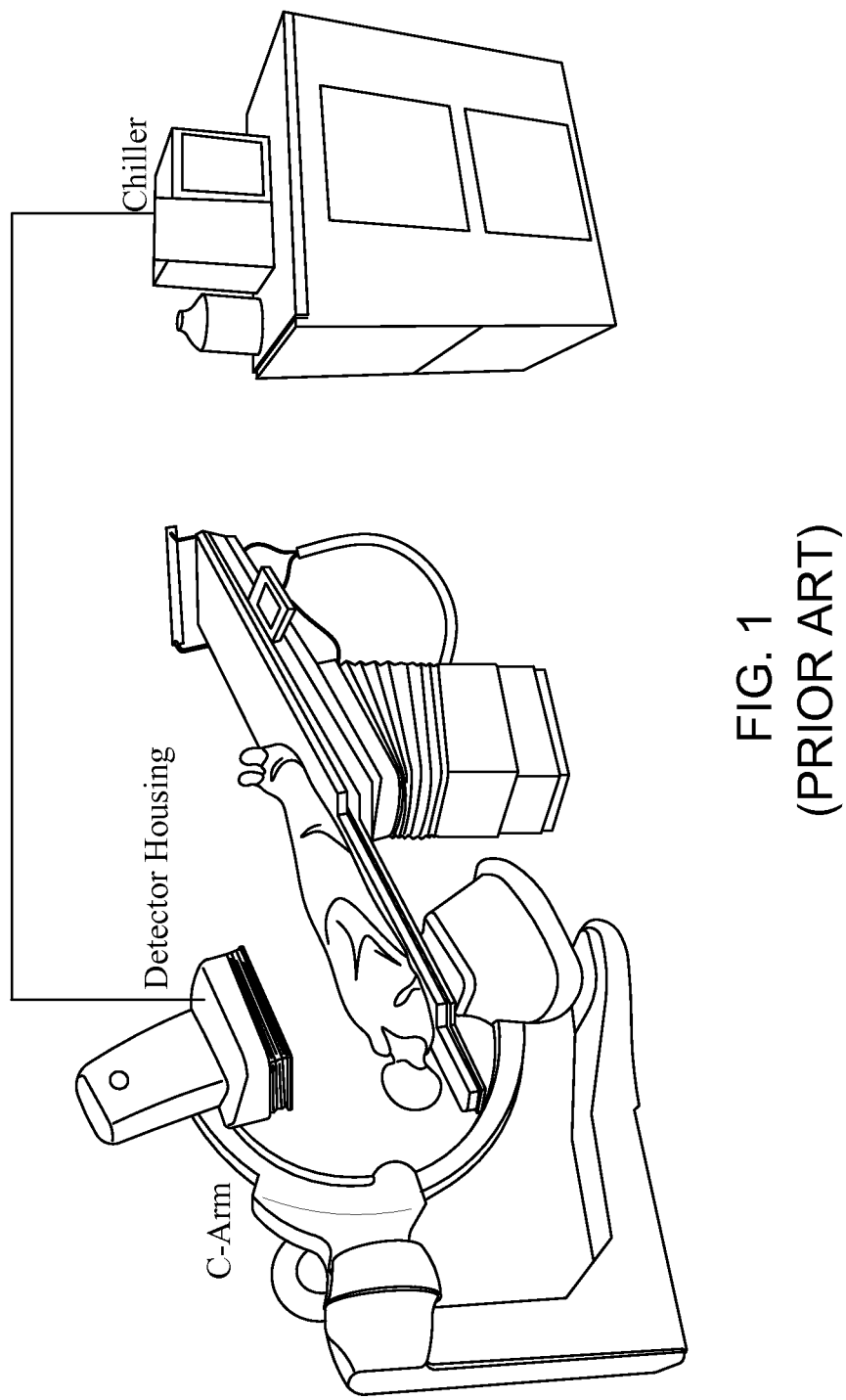
FIG. 1 exhibits an existing interventional imaging system, which uses a chiller for cooling.

FIG. 1 exhibits an existing interventional imaging system, which interventional imaging system uses a chiller for cooling.

Figure 2:
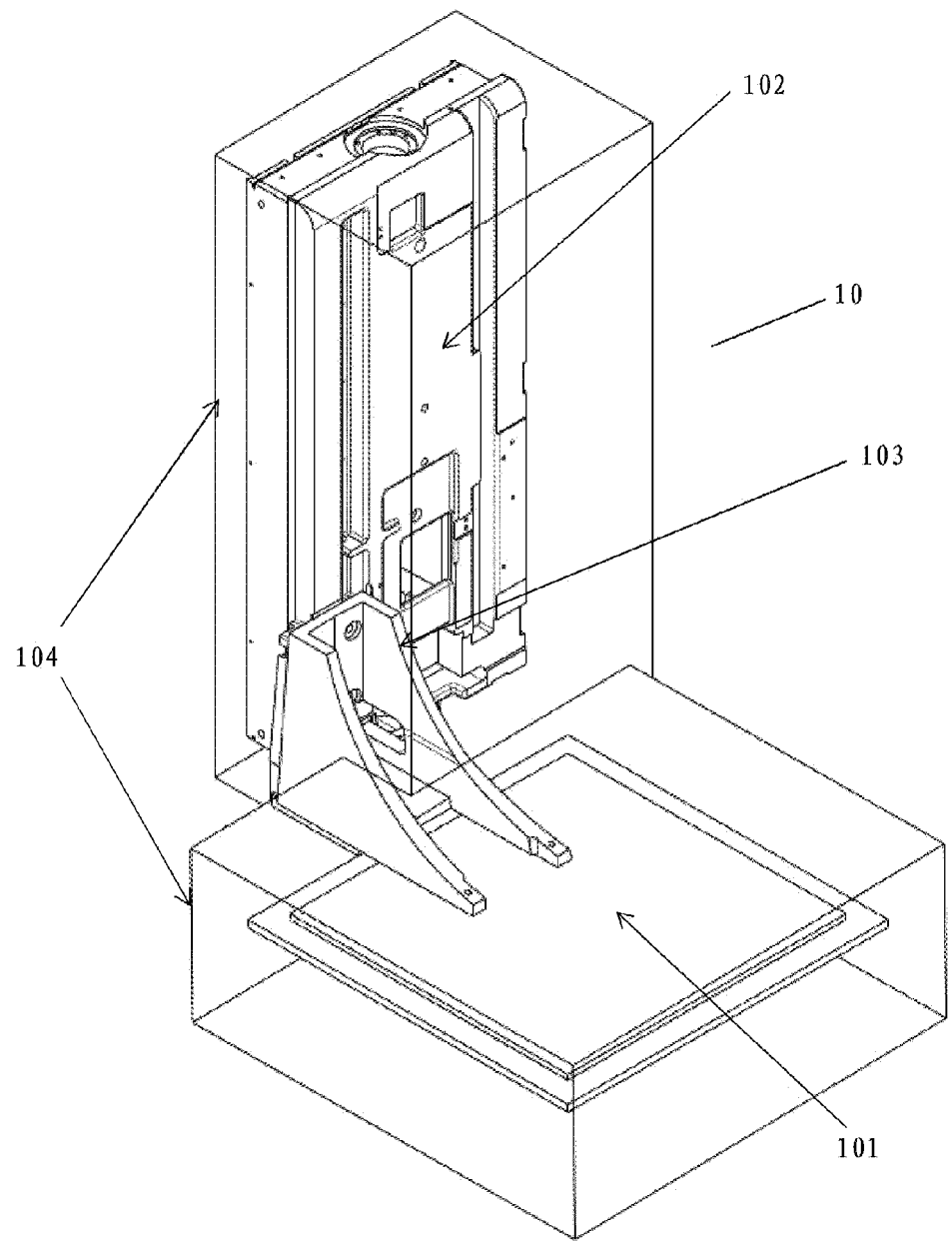
FIG. 2 is a schematic diagram showing a configuration of a detector housing according to an embodiment of the present invention.

FIG. 2 is a schematic diagram showing a configuration of a detector housing. The detector housing is designated at a reference 10, and mainly comprises the following mechanical components: a detector tray 101 to which the detector is attached; a lift frame 102 on which a driving mechanism is installed to lift up/down the detector housing 10; a connecting arm 103 to connect the detector tray 101 and the lift frame 102; and a cover 104 to shield the detector and the components thereof from other external objects.

In an embodiment, the driving mechanism for lifting up/down the detector housing 10 can be a threaded shaft/rail/motor assembly. However, in some embodiments, the driving mechanism can be in any other suitable forms.

In an embodiment, the connecting arm is a L-arm 103. However, in some embodiments, the connecting arm can be in any other suitable forms.

In an embodiment, the cover 104 can be a PC cover. However, in some embodiments, the cover of the detector housing can also be made of any other suitable material.

Figure 3:
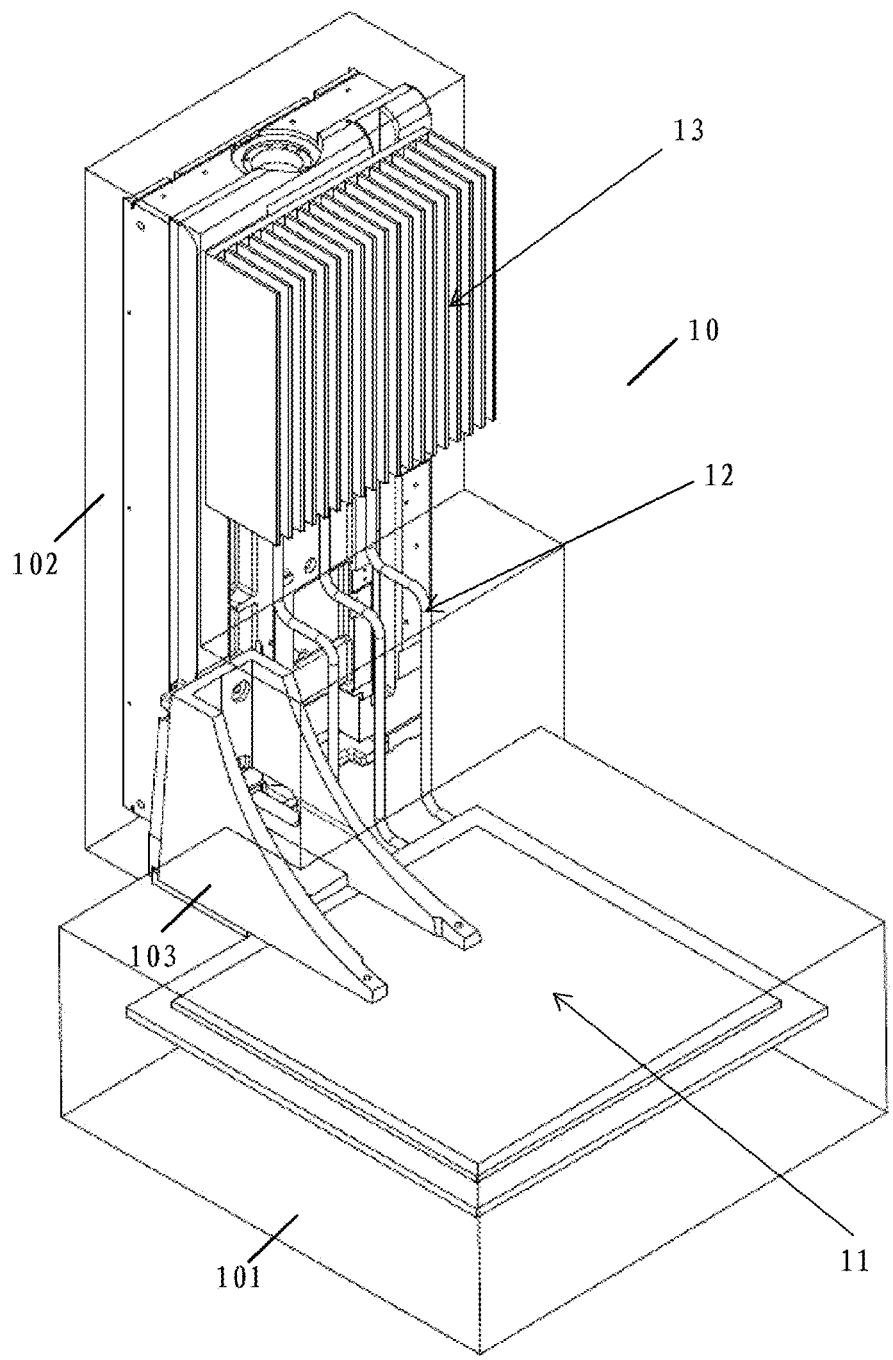
FIG. 3 is a schematic diagram of a cooling system for realizing a cooling method according to an embodiment of the present invention, the cooling system using a heat pipe and an external heat sink in the detector housing.

FIG. 3 is a schematic diagram of a cooling system for an interventional detector according to an embodiment the present invention, the cooling system using a heat pipe and an external heat sink in the detector housing.

In an embodiment, the cooling system comprises: a heat pipe 12 which connects the detector tray 101 and the lift frame 102 so as to reduce a thermal resistance $R_{arm}$ therebetween and transfer more heat from the detector; an external heat sink 13 connected with the heat pipe 12 for reducing a thermal resistance $R_{lift}$ between the lift frame 102 and an ambient environment; and a high heat transfer coefficient (K) device 11 embedded into the detector tray 101 for collecting heat leading to the heat pipe 12, obtaining a uniform temperature distribution, and reducing a thermal resistance $R_{tray}$ of the detector tray.

In an embodiment, the high heat transfer coefficient device 11 is a vapor chamber 11. However, persons skilled in the art should appreciate that the high heat transfer coefficient device 11 can also be other devices comprising high heat transfer coefficient materials.

In an embodiment, the heat pipe 12, the external heat sink 13 and the high heat transfer coefficient device 11 can be fabricated into one thermal module.

With this configuration of the system, the following cooling method can be employed to cool the detector, wherein the cooling method comprises: using the heat pipe 12 to connect the detector tray 101 and the lift frame 102 so as to reduce the thermal resistance $R_{arm}$ therebetween and transfer more heat from the detector; using the external heat sink 13 connected with the heat pipe 12 so as to reduce the thermal resistance $R_{lift}$ between the lift frame 102 and the ambient environment; and embedding the high heat transfer coefficient device 11 (the vapor chamber 11 or other devices comprising high heat transfer coefficient materials) into the detector tray 101 so as to collect heat leading to the heat pipe 12, obtain a uniform temperature distribution, and reduce the thermal resistance $R_{tray}$ of the detector tray.

Similarly, in an embodiment, the heat pipe 12, the external heat sink 13 and the high heat transfer coefficient device 11 can be fabricated into one thermal module.

Figure 4:
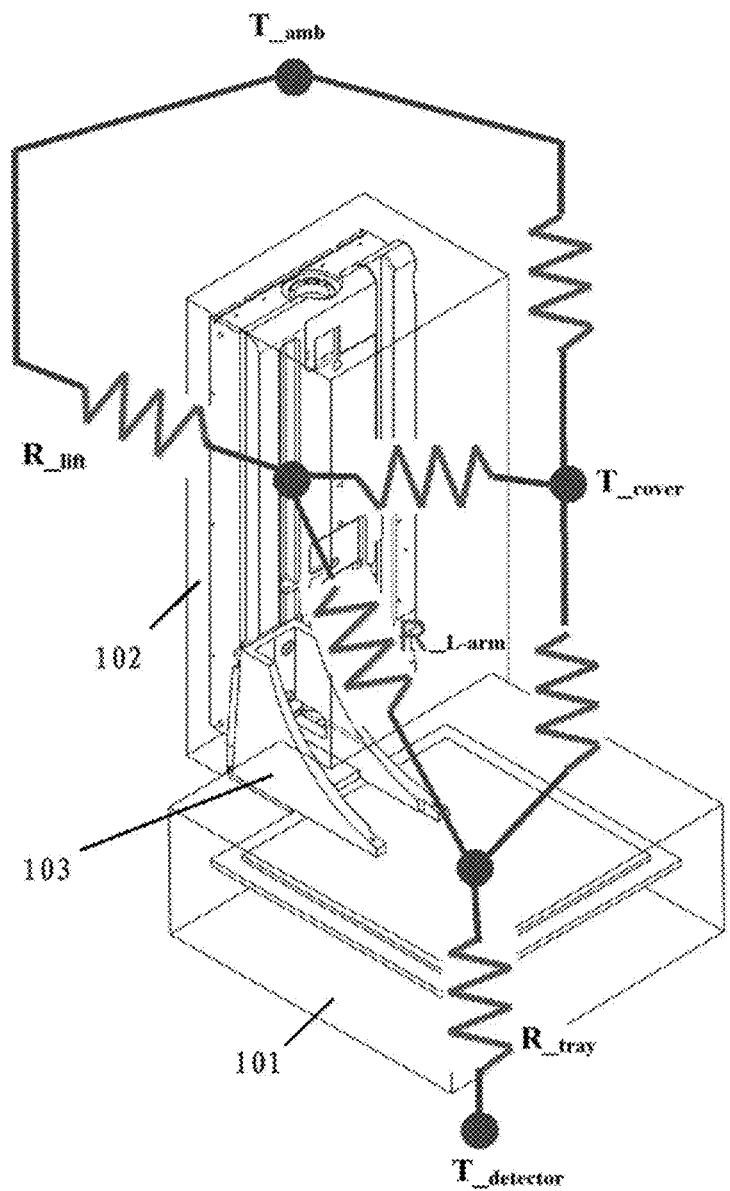
FIG. 4 is a heat circuit diagram of the cooling system as shown in FIG. 3 according to an embodiment of the present invention.

FIG. 4 is a heat circuit diagram of the cooling system as shown in FIG. 3. As known by referring to the configuration of the system and the heat circuit diagram of FIG. 4, through internal optimization of the detector housing, cooling of the detector can be realized using air natural convection. Thermal capacity of system is increased due to the inclusion of an external heat sink, which will benefit thermal transient performance.

Figure 8:
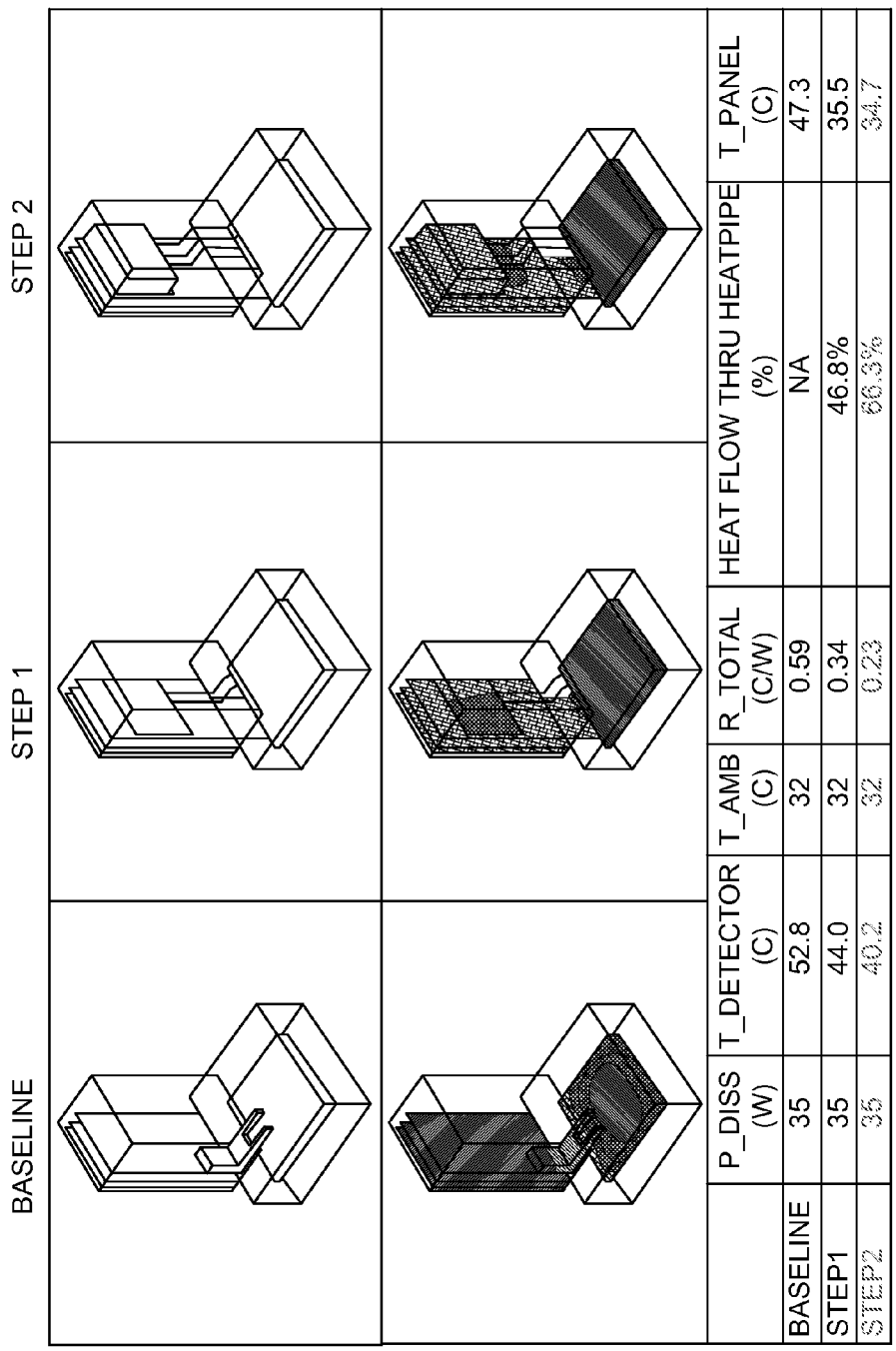
FIG. 8 is a schematic diagram of a CFD simulation as obtained when cooling by utilizing a method according to an embodiment of the present invention.

FIG. 8 is a schematic diagram of CFD simulation as obtained when cooling by utilizing the method. Wherein, the row of Baseline shows conventional design data as obtained when cooling is conducted without employing the method according to embodiments of the present invention; the row of STEP 1 shows data as obtained in the case wherein only the heat pipe 12 is employed without using the external heat sink 13; the row of STEP 2 shows simulation cooling data as realized by the cooling method of the present invention in the case wherein both the heat pipe 12 and the external heat sink 13 are employed. As seen from the figure, simulation temperature of detector panel (34.7° C.), as obtained by employing embodiments of the present invention, is substantially lowered when compared with the panel temperature (47.3° C.) in the conventional design without employing embodiments of the present invention, and completely meets related thermal requirements.

Figure 5:
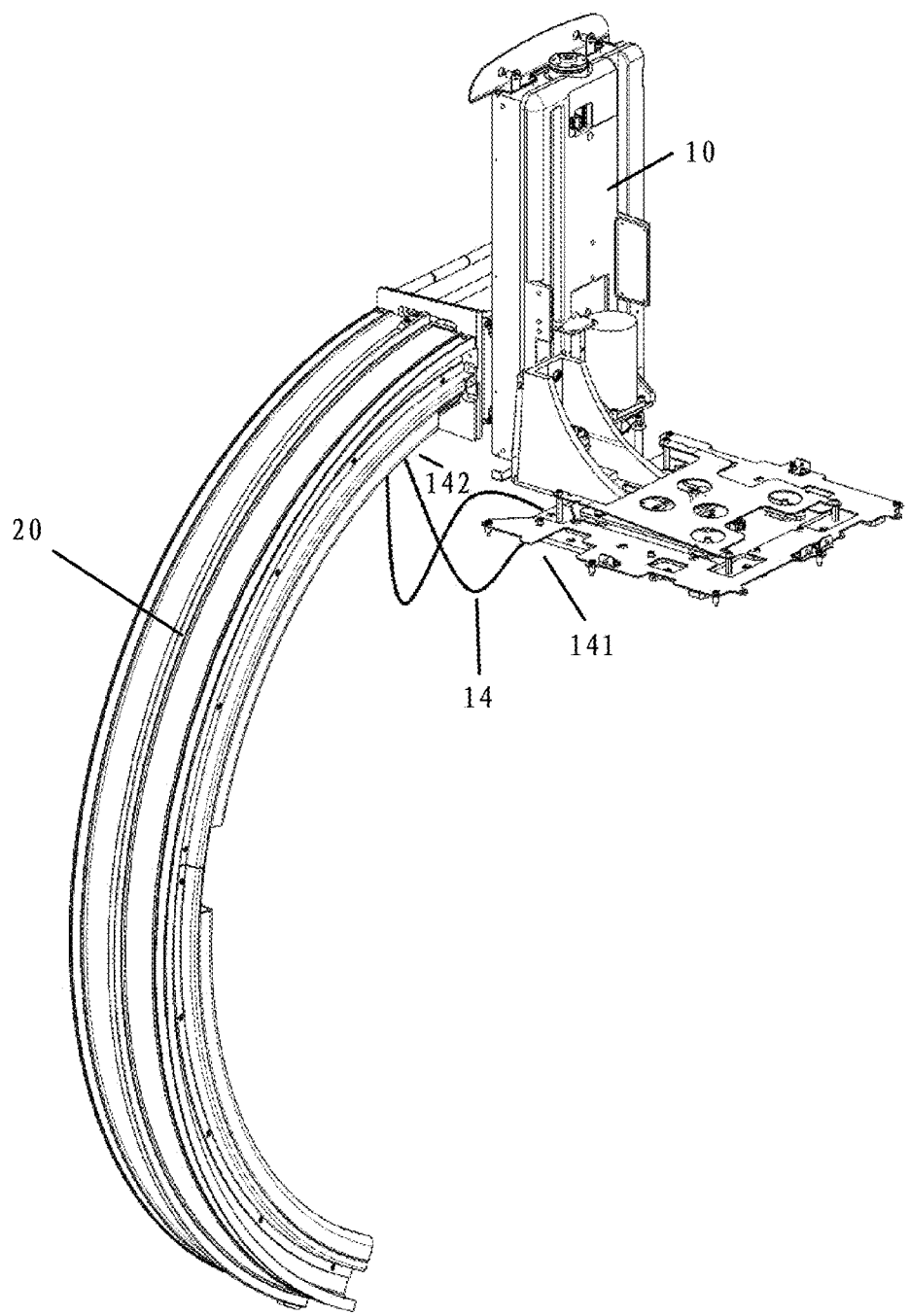
FIG. 5 is a schematic diagram of a cooling system for realizing a cooling method according to an embodiment of the present invention, the cooling system using a loop heat pipe between the detector housing and a C-arm.

FIG. 5 is a schematic diagram of another cooling system for an interventional detector according to an embodiment of the present invention, the cooling system using a loop heat pipe 14 between the detector housing 10 and the C-arm 20.

In an embodiment, the cooling system comprises a loop heat pipe (LHP) 14 connected between the detector tray 101 and the C-arm 20 of an interventional imaging system, the loop heat pipe LHP14 comprising a condenser end 141 and an evaporator end 142, wherein the condenser end 141 of the LHP14 is embedded into the detector tray 101; the evaporator end 142 of the LHP14 is embedded into a heatspreader (e.g., a copper heatspreader) which is fixed onto the C-arm.

Wherein, the detector housing 10 and the C-arm 20 can work as two heat sinks in parallel.

In an embodiment, the C-arm 20 can be made of A1 6063 (thermal conductivity: 200 W/m-K) and has large heat transfer area. However, persons skilled in the art should appreciate that in other embodiments, the C-arm 20 can be made of any other suitable material.

With this configuration of the system, the following cooling method can be employed to cool the detector, wherein the cooling method comprises: using the loop heat pipe (LHP)14 as a high-efficiency cooling path to connect the detector tray 101 and the C-arm 20 of an interventional imaging system, the loop heat pipe LHP14 comprising the condenser end 141 and the evaporator end 142; embedding the condenser end 141 of the LHP14 onto the detector tray 101; embedding the evaporator end 142 of the LHP14 into the heatspreader (e.g., a copper heatspreader) which is fixed onto the C-arm, wherein the detector housing 10 and the C-arm 20 work as two heat sinks in parallel.

By using the C-arm 20 as a heat sink, cooling is realized through air natural convection. In addition, thermal capacity of system is increased due to the inclusion of the C-arm 20, which will benefit thermal transient performance.

Figure 6:
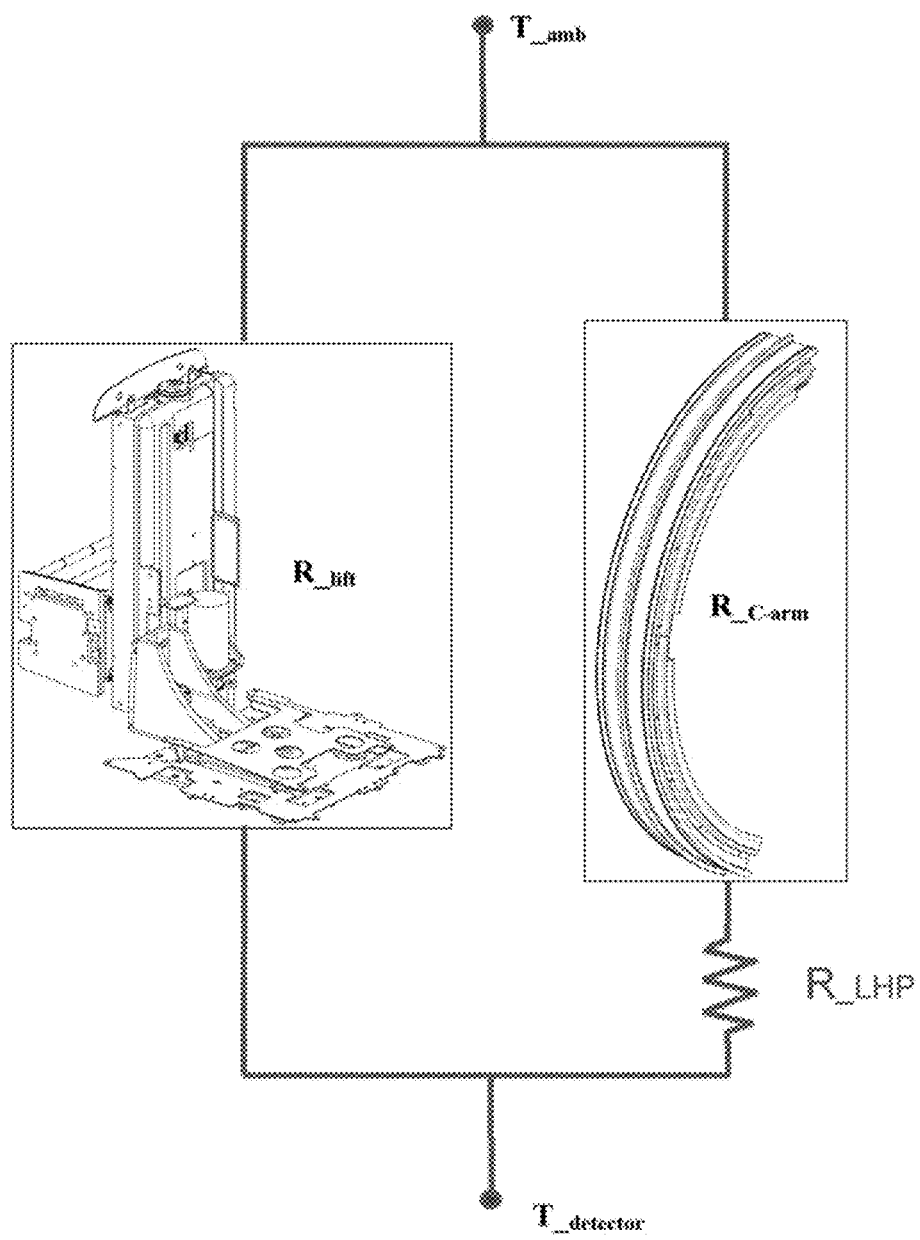
FIG. 6 is a heat circuit diagram of the cooling system as shown in FIG. 5 according to an embodiment of the present invention.

FIG. 6 is a heat circuit diagram of the cooling system as shown in FIG. 5.

Figure 7:
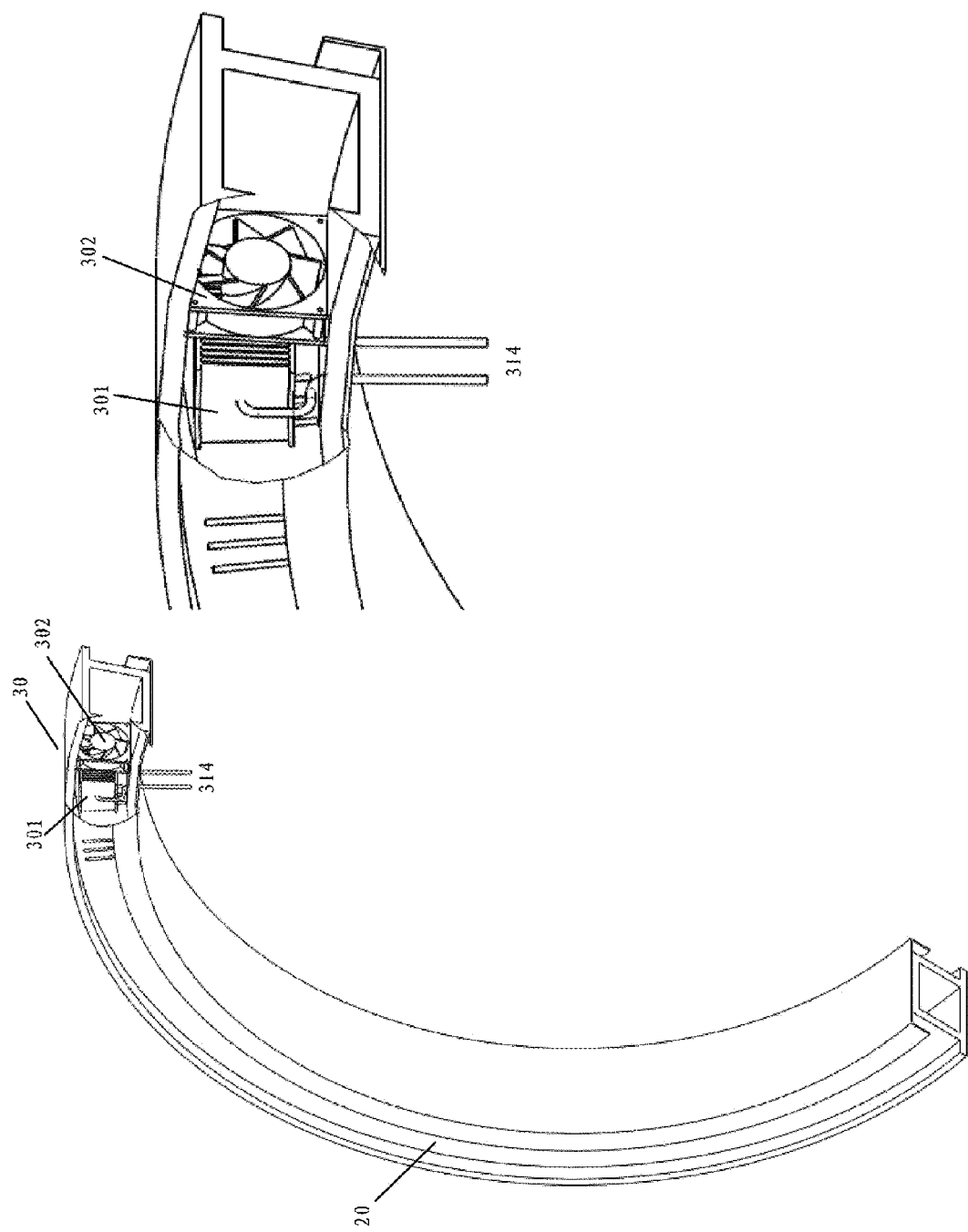
FIG. 7 is a schematic diagram of a cooling system for realizing a cooling method according to an embodiment of the present invention, the cooling system using a fan/heat sink/loop heat pipe module in the C-arm.

FIG. 7 is a schematic diagram of a further cooling system for an interventional detector according to an embodiment of the present invention, the cooling system using a fan/heat sink/loop heat pipe module 30 in the C-arm. Wherein, the fan/heat sink/loop heat pipe module 30 comprises a fan 302 which is hidden in the C-arm 20 of the interventional imaging system, so as to form air forced convection. The loop heat pipe (LHP) 314 in the fan/heat sink/loop heat pipe module 30 is still used as a thermal connector between the detector and the C-arm 20. The fan/heat sink/loop heat pipe module 30 further comprises a heat sink 301. The condenser end of the LHP314 is embedded into the detector tray 101; the evaporator end of the LHP314 is embedded into the heat sink 301. An air vent is opened at a proper place on the C-arm 20 where it is safe for a patient.

With this configuration of the system, the following cooling method can be employed to cool the interventional detector, which cooling method comprises: using the fan/heat sink/loop heat pipe module 30 which is fixed in the C-arm 20 of the interventional imaging system by utilizing an existing pipe structure as a flow tunnel, and hiding the fan 302 of the module 30 in the C-arm 20, so as to form air forced convection; using the LHP314 of the fan/heat sink/loop heat pipe module 30 as a thermal connector between the detector and the C-arm 20, wherein the condenser end of the LHP314 is embedded into the detector tray 101, and the evaporator end of the LHP314 is embedded on the heat sink 301 of the fan/heat sink/loop heat pipe module 30; and opening an air vent at a proper place on the C-arm 20 where it is safe for a patient.

In an embodiment, speed of the fan 302 can be adjusted per a thermal requirement.

TEC can be introduced if necessary.

By using the heat pipe 12 and/or the loop heat pipe 14 in the cooling system and corresponding method as described above, embodiments of the present invention at least realize the following advantages: new application for interventional detector cooling, passive and silent; high reliability, no moving part or electronics or water pipe system; no additional power consumption for cooling; and cost saving. In addition, by using the fan/heat sink/loop heat pipe module 30 which is fixed in the C-arm 20, embodiments of the present invention can also realize the following further advantageous effects: higher heat density; controllable temperature; and lower noise.

While exemplary embodiments of the present invention have been discussed in the present application, persons skilled in the art will appreciate that various changes, omissions and/or additions can be made, and equivalents can replace their components, without departing from the spirits and scope of the present invention. In addition, many modifications may be made to adapt a particular situation or material to the teachings of the present invention without departing from the scope of the present invention. Therefore, it is intended that the present invention is not limited to the particular embodiment disclosed as the best mode contemplated for carrying out the present invention, but that the invention will include all embodiments that fall within the scope of the appended claims. Furthermore, unless indicated otherwise, the usage of such terms as "first" and "second" does not indicate any sequence or importance; on the contrary, such terms as "first" and "second" are used to distinguish one element from another.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural element with insubstantial differences from the literal languages of the claims.

What is claimed is:

1. A cooling system for cooling an interventional detector comprising a detector housing, the detector housing comprising a detector tray to which the detector is attached, a lift frame on which a driving mechanism is installed to lift up/down the detector housing, a connecting arm connecting the detector tray and the lift frame, and a cover shielding the detector and other components from other external objects, the cooling system comprising:
 a heat pipe connecting the detector tray and the lift frame, wherein the heat pipe is configured to reduce a thermal resistance between the detector tray and the lift frame and to transfer more heat from the detector;
 an external heat sink connected with the heat pipe, wherein the external heat sink is configured to reduce a thermal resistance between the lift frame and the ambient environment; and
 a heat transfer coefficient device embedded into the detector tray, wherein the heat transfer coefficient device is a vapor chamber configured to collect heat leading to the heat pipe, obtain a uniform temperature distribution, and reduce a thermal resistance of the detector tray.

2. The system of claim 1, wherein the heat pipe, the external heat sink, and the heat transfer coefficient device are integrated into one thermal module.

3. The system of claim 1, wherein the heat pipe is a loop heat pipe connecting the detector tray and a C-arm of an interventional imaging system, wherein one end of the loop heat pipe is embedded into the detector tray and the opposite end of the loop heat pipe is embedded into a heatspreader fixed onto the C-arm.

4. The system of claim 3, wherein the lift frame and the C-arm are configured to operate as two separate heat sinks in parallel.

5. The system of claim 3, wherein the C-arm comprises Al-6063 with a thermal conductivity of 200 W/m-K.

6. The system of claim 3, further comprising:
 a cooling module fixed in a C-arm of an interventional imaging system, the cooling module comprising a fan hidden in the C-arm of the interventional imaging system, a loop heat pipe as a thermal connector between the detector and the C-arm, and a heat sink, wherein a condenser end of the loop heat pipe is embedded into the detector tray, and an evaporator end of the loop heat pipe is embedded into the heat sink; and
 an air vent located at a location on the C-arm, wherein the location is safe for a patient.

7. The system according to claim 6, wherein a speed of the fan is adjusted according to a thermal requirement.

* * * * *